United States Patent
Carmi

(10) Patent No.: US 9,600,877 B2
(45) Date of Patent: Mar. 21, 2017

(54) QUANTITATIVE IMAGING

(71) Applicant: KONINKLIJKE PHILIPS N.V., Eindhoven (NL)

(72) Inventor: Raz Carmi, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 38 days.

(21) Appl. No.: 14/649,723

(22) PCT Filed: Dec. 16, 2013

(86) PCT No.: PCT/IB2013/060995
§ 371 (c)(1),
(2) Date: Jun. 4, 2015

(87) PCT Pub. No.: WO2014/097124
PCT Pub. Date: Jun. 26, 2014

(65) Prior Publication Data
US 2016/0217566 A1    Jul. 28, 2016

Related U.S. Application Data

(60) Provisional application No. 61/739,896, filed on Dec. 20, 2012.

(51) Int. Cl.
*G06K 9/00* (2006.01)
*G06T 7/00* (2006.01)
(Continued)

(52) U.S. Cl.
CPC ............ *G06T 7/0012* (2013.01); *A61B 6/032* (2013.01); *G06T 5/002* (2013.01); *G06T 5/007* (2013.01);
(Continued)

(58) Field of Classification Search
CPC combination set(s) only.
See application file for complete search history.

(56) References Cited

U.S. PATENT DOCUMENTS 6,466,687 B1    10/2002   Uppaluri et al.
2009/0232269 A1*  9/2009   Hsieh ................ A61B 6/032
                                              378/5
(Continued)

FOREIGN PATENT DOCUMENTS

WO         2012151579 A2     11/2012

OTHER PUBLICATIONS

Ganeshan, B., et al.; Dynamic texture analysis of contrast enhanced CT; 2009; European Journal of Radiology; 70 (1)101-110.
(Continued)

*Primary Examiner* — Alex Liew

(57) ABSTRACT

The following generally relates to scaling irregularity maps based at least on one of a histogram bin width, an image noise or a contrast agent concentration. A method includes obtaining a non-scaled irregularity map generated based on local weighted histograms of voxel distributions about voxels of interest from volumetric image data of a subject or object. The local weighted histograms include a plurality of bins having a predetermined bin width. The local weights are determined based on a predetermined cluster length. The method further includes scaling the non-scaled irregularity map, generating a scaled irregularity map. The non-scaled irregularity map is scaled based at least on the histogram bin width.

20 Claims, 6 Drawing Sheets

(51) Int. Cl.
 G06T 5/00 (2006.01)
 G06T 5/40 (2006.01)
 A61B 6/03 (2006.01)
(52) U.S. Cl.
 CPC .............. *G06T 5/40* (2013.01); *G06T 7/0081* (2013.01); *G06T 2207/30004* (2013.01)

(56) References Cited

U.S. PATENT DOCUMENTS

| | | |
|---|---|---|
| 2009/0324049 A1 | 12/2009 | Kontos et al. |
| 2010/0142775 A1 | 6/2010 | Ganeshan et al. |
| 2010/0266179 A1 | 10/2010 | Ramsay et al. |
| 2011/0234765 A1* | 9/2011 | Tanaka ............... H04N 13/0018 348/47 |
| 2011/0280457 A1 | 11/2011 | Nielsen et al. |
| 2013/0148884 A1* | 6/2013 | Lee .................... G06K 9/00758 382/165 |

OTHER PUBLICATIONS

Ganeshan, B., et al.; Texture analysis of non-small cell lung cancer on unenhanced computed tomography: initial evidence for a relationship with tumour glucose metabolism and stage; 2010; Cancer Imaging; 10:137-143.
Ganeshan, B., et al.; Three-dimensional textural analysis of brain images reveals distributed grey-matter abnormalities in schizophrenia; 2010; European Radiology; 20(4)941-948.
Ganeshan, B., et al.; Tumour heterogeneity in oesophageal cancer assessed by CT texture analysis: Preliminary evidence of an association with tumour metabolism, stage, and survival; 2012; Clinical Radiology; 67(2)157-164.
Ganeshan, B., et al.; Tumor heterogeneity in non-small cell lung carcinoma assessed by CT texture analysis: a potential marker of survival; 2012; European Radiology; 22(4)796-802.
Goh, V., et al.; Assessment of Response to Tyrosine Kinase Inhibitors in Metastatic Renal Cell Cancer: CT Texture as a Predictive Biomarker; 2011; Radiology; 261(1)165-171.
Kadir, T., et al.; Saliency, Scale and Image Description; 2001; International Journal of Computer Vision; 45(2)83-105.
Liang, M.; 3D co-occurrence matrix based texture analysis applied to cervical cancer screening; 2012; Uppsala Universitet; http://urn.kb.se/resolve?urn=urn.nbn:se:uu:diva-180850; 39 pages.
Miles, K. A., et al.; Colorectal Cancer: Texture Analysis of Portal Phase Hepatic CT Images as a Potential Marker of Survival; 2009; Radiology; 250(2)444-452.
Miles, K.; Quantitative imaging biomarkers for computed tomography; 2012; RAD Magazine; 38(440)11-12.
Mishima, M., et al.; Quantitative assessment of the spatial distribution of low attenuation areas on X-ray CT using texture analysis in patients with chronic pulmonary emphysemia; 1997; Frontiers of Medical and Biological Engineering; 8(1)19-34.
Mitrea, D., et al.; Abdominal Tumor Characterization and Recognition Using Superior-Order Cooccurrence Matrices, Based on Ultrasound Images; 2012; Computational and Mathematical Methods in Medicine; ID#348135; 17 pages.
Pang, Y., et al.; Computerized Segmentation and Characterization of Breast Lesions in Dynamic Contrast-Enhanced MR Images Using Fuzzy c-Means Clustering and Snake Algorithm; 2012; Computational and Mathematical Methods in Medicine; ID#634907; 10 pages.
Sanghera, B., et al.; Reproducibility of 2D and 3D Fractal analysis Techniques for the Assessment of Spatial Heterogeneity of Regional Blood Flow in Rectal Cancer; 2012; Radiology; 263(3)865-873.
Skogen, K., et al.; Imaging heterogeneity in gliomas using texture analysis; 2011; Cancer Imaging; 11:AS113.
Sorensen, L., et al.; Quantitative Analysis of Pulmonary Emphysema Using Local Binary Patterns; 2010; IEEE Trans. on Medical Imaging; 29(2)559-569.
TexRAD Company Website; www.texrad.org; TexRAD Texture Analysis; downloaded Jan. 9, 2013.
Wachinger, C., et al.; Structural Image Representation for Image Registration; 2010 IEEE Conference on Computer Vision and Pattern Recognition; pp. 23-30.
Wallis, K. F.; A note on the calculation of entropy from histograms; 2006; University of Warwick; recovered from the internet; http://www2.warwick.ac.uk/fac/soc/economics/staff/academic/wallis/publications/entropy.pdf.
Xu, L., et al.; An Information-Theoretic Framework for Flow Visualization; 2010; IEEE Trans. on Visualization and Computer Graphics; 16(6)1216-1224.

* cited by examiner

QUANTITATIVE IMAGING

CROSS REFERENCE TO RELATED APPLICATIONS

This application is a national filing of PCT application Serial No. PCT/IB2013/060995, filed Dec. 16, 2013, published as WO 2014/097124 A2 on Jun. 26, 2014, which claims the benefit of U.S. provisional application Ser. No. 61/739,896 filed Dec. 20, 2012, which is incorporated herein by reference.

The following generally relates to quantitative imaging and more particularly to tissue irregularity maps, and is described with particular application to computed tomography (CT); however, the following is also amenable to other imaging modalities.

Visual analysis of diagnostic images has been based on evaluating morphological information such as size and shape. Image perception such as identifying relationships between perceived patterns and possible diagnosis have depended on a radiologist's knowledge, analytical skills, memory, intuition, and diligence. However, the human visual sensory system has difficulties in discriminating textural information such as coarseness and irregularity that result from local spatial variations in image brightness or contrast. Textural or structural analysis has been a component of computer-assisted diagnosis (CAD).

CAD algorithms have included an initial quantification using mathematical descriptors of texture computed from different available texture analysis approaches followed by use of decision algorithms based on computer vision and artificial intelligence, machine learning, or artificial neural networks. Texture quantification approaches that are known in the literature can be divided into several general categories: A) model based approach such as fractal and stochastic models, which analyze texture by identifying an appropriate model that reflects prior information about the type of tissue images to be analyzed; B) frequency domain power spectrum analysis, structural shape fitting methods, or wavelet analysis, and C) histogram based and statistical based analysis.

Clinical studies have suggested that CT texture analysis may yield practical predictive and prognostic information in patients with non-small cell lung cancer, colorectal cancer, renal cell cancer, and liver metastasizes. The physiological rationales are that tissue heterogeneity and irregularity, such as those that exist frequently in the tumor blood supply, is a well-recognized feature of malignancy. Particularly it was shown that histogram-based entropy and uniformity calculation can be used to assess the distribution of texture coarseness and irregularity within or around a lesion, while trying to reduce the influence of image noise texture. Texture analysis has been demonstrated as well for non-cancer diseases such as lung emphysema.

Nevertheless, current approaches are not well-suited for robust quantitative analysis of tissue textures and structures in image data. For example, such approaches have provided relative arbitrary results that can be difficult to count on when comparing different clinical cases or when trying to set general treatment guidelines, have depended on complicated models or databases of training sets, have required many parameters that should be selected and optimized for the particular clinical case, have required accurate ROI delineation by the user or sophisticated segmentation algorithms, etc. As such, there is an unresolved need for other approaches.

Aspects described herein address the above-referenced problems and others.

The following generally relates to scaling irregularity maps based at least on one of a histogram bin width, an image noise or a contrast agent concentration.

In one aspect, a method includes obtaining a non-scaled irregularity map generated based on local weighted histograms of voxel distributions about voxels of interest from volumetric image data of a subject or object. The local weighted histograms include a plurality of bins having a predetermined bin width. The local weights are determined based on a predetermined cluster length. The method further includes scaling the non-scaled irregularity map, generating a scaled irregularity map. The non-scaled irregularity map is scaled based at least on the histogram bin width.

In another aspect, an image data processing system includes a scaled irregularity map generator that obtains a non-scaled irregularity map generated based on local weighted histograms of voxel distributions about voxels of interest from volumetric image data of a subject or object. The local weighted histograms include a plurality of bins having a predetermined bin width, and wherein the local weights are determined based on a predetermined cluster length. The scaled irregularity map generator includes a histogram bin-width scaler that scales the non-scaled irregularity map, generating a scaled irregularity map, wherein the non-scaled irregularity map is scaled based at least on one of the histogram bin width, an image noise or a contrast agent concentration.

In another aspect, a computer readable storage medium is encoded with one or more computer executable instructions, which, when executed by a processor of a computing system, causes the processor to: scale a non-scaled irregularity map, generating a scaled irregularity map, wherein the non-scaled irregularity map is scaled based at least on one of the histogram bin width, an image noise or a contrast agent concentration and the scaled irregularity map is represented via one or more of an entropy or an inverse of uniformity of the local weighted histogram, or high-order statistics of local weighted high-order histogram.

The invention may take form in various components and arrangements of components, and in various steps and arrangements of steps. The drawings are only for purposes of illustrating the preferred embodiments and are not to be construed as limiting the invention.

FIG. 1 schematically illustrates an example image data processing system in connection with an imaging system.

FIG. 2 schematically illustrates an example of the image data processing system of FIG. 1.

Figure 1:
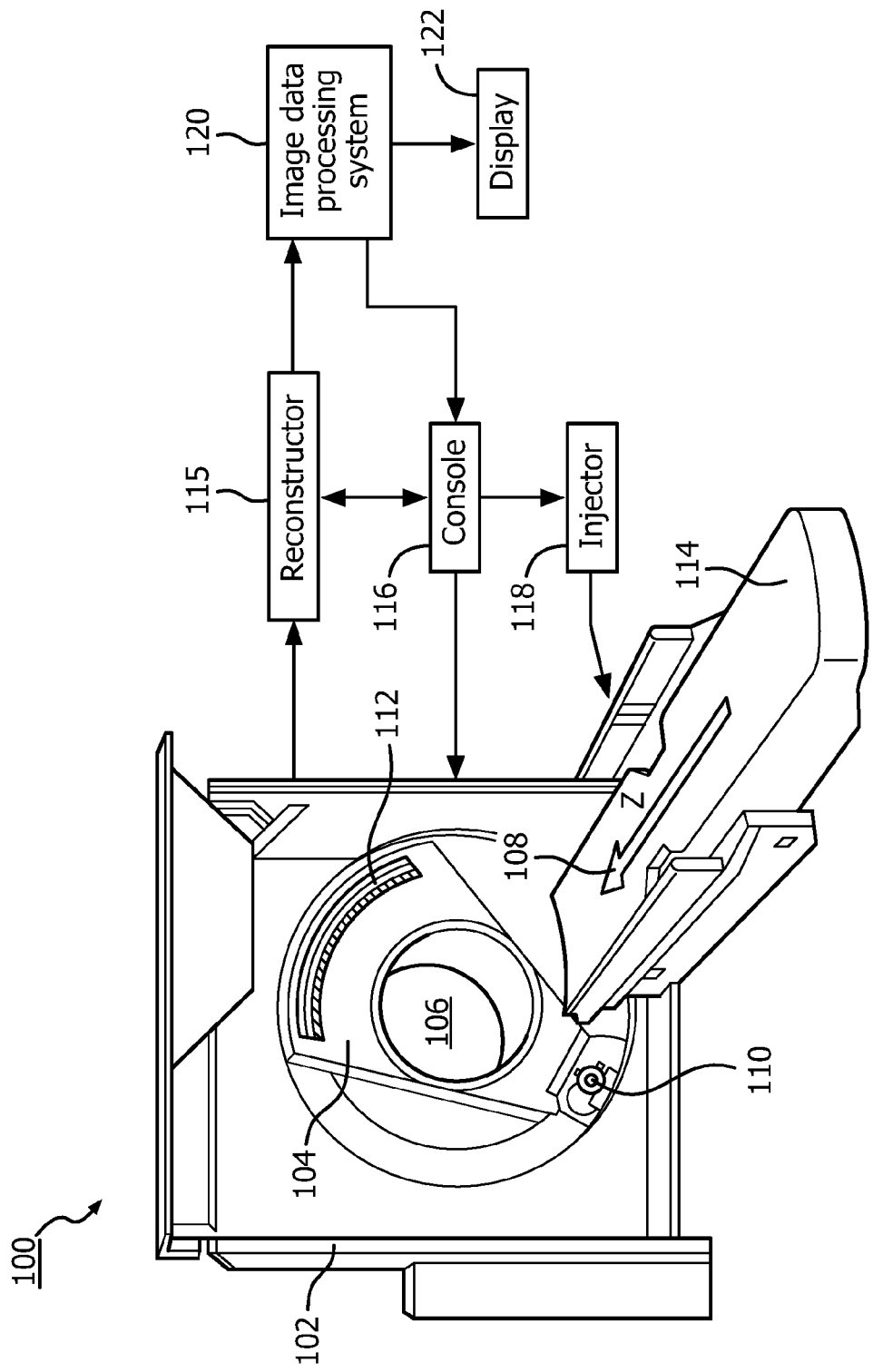

FIG. 1 schematically illustrates an example imaging system 100 such as a CT scanner. In other embodiments, the imaging system 100 may include one or more of an MII, PET, SPECT, Ultrasound, and/or other imaging system. The illustrated imaging system 100 includes a stationary gantry 102 and a rotating gantry 104, which is rotatably supported by the stationary gantry 102 and rotates around an examination region 106 about a z-axis 108.

A radiation source 110, such as an x-ray tube, is rotatably supported by the rotating gantry 104, rotates with the rotating gantry 104, and emits polychromatic radiation that traverses the examination region 106. A radiation sensitive detector array 112 subtends an angular arc opposite the radiation source 110 across the examination region 106, detects radiation traversing the examination region 106, and generates a signal indicative thereof.

A subject support 114 supports an object or subject in the examination region 106 before, during and/or after scanning. A reconstructor 115 reconstructs the projection data, generating volumetric image data. Such data can be dynamic or non-dynamic data. A general-purpose computer serves as an operator console 116. Software resident on the console 116 allows the operator to interact with the scanner 100. Such interaction includes, but is not limited to selecting a scan protocol, initiating scanning, etc.

An optional injector 118 is configured to administer one or more contrast material or agents, e.g., for a contrast enhanced imaging procedure. The injector 118 can be controlled by way of the imaging system 100 and/or manually by a clinician. The contrast material can alternatively be manually administered by the clinician or the like. Where the contrast material is manually administered or where no contrast material is administered, the injector 118 can be omitted.

An image data processing system 120 processes image data and generates, at least, a scaled tissue irregularity map based thereon. As described in greater detail below, in one non-limiting instance, this includes employing a local histogram entropy approach to generate a non-scaled irregularity map and then scaling the non-scaled irregularity map to produce an absolute irregularity measure with respect to bin width, image noise levels and/or contrast agent concentrations. The scaled irregularity map can be visually presented via a display 122 and/or otherwise utilized.

The scaled irregularity map can be used to facilitate identifying a presence of disease with irregular tissue patterns, without considering a disease model, such as cancer and/or other disease with irregular tissue patterns. A non-scaled irregularity map can also be visually presented, alone or in combination with the scaled irregularity map. This approach can be used, for example, with CT, MR, etc. studies such as tumor follow-up, even if the scan is performed with a very different scanning and imaging conditions. In addition, a quantitative diagnosis may be compared against potential treatment guidelines.

The processed image data can be generated by the imaging system 100 and/or other imaging system and/or obtained from the imaging system 100 and/or storage medium, such as portable memory, a server, a database, a radiology information system (RIS), hospital information system (HIS), an electronic medical record (EMR), picture archive and communication system (PACS), and/or other data repository The image data processing system 120 can be implemented via one or more processors of one or more computing systems executing one or more computer readable instructions embedded, encoded, etc. on computer readable storage medium such as physical memory and/or other non-transitory medium. Additionally or alternatively, at least one of the computer readable instructions can be carried by a carrier wave, signal, and/or other transitory medium.

Figure 2:
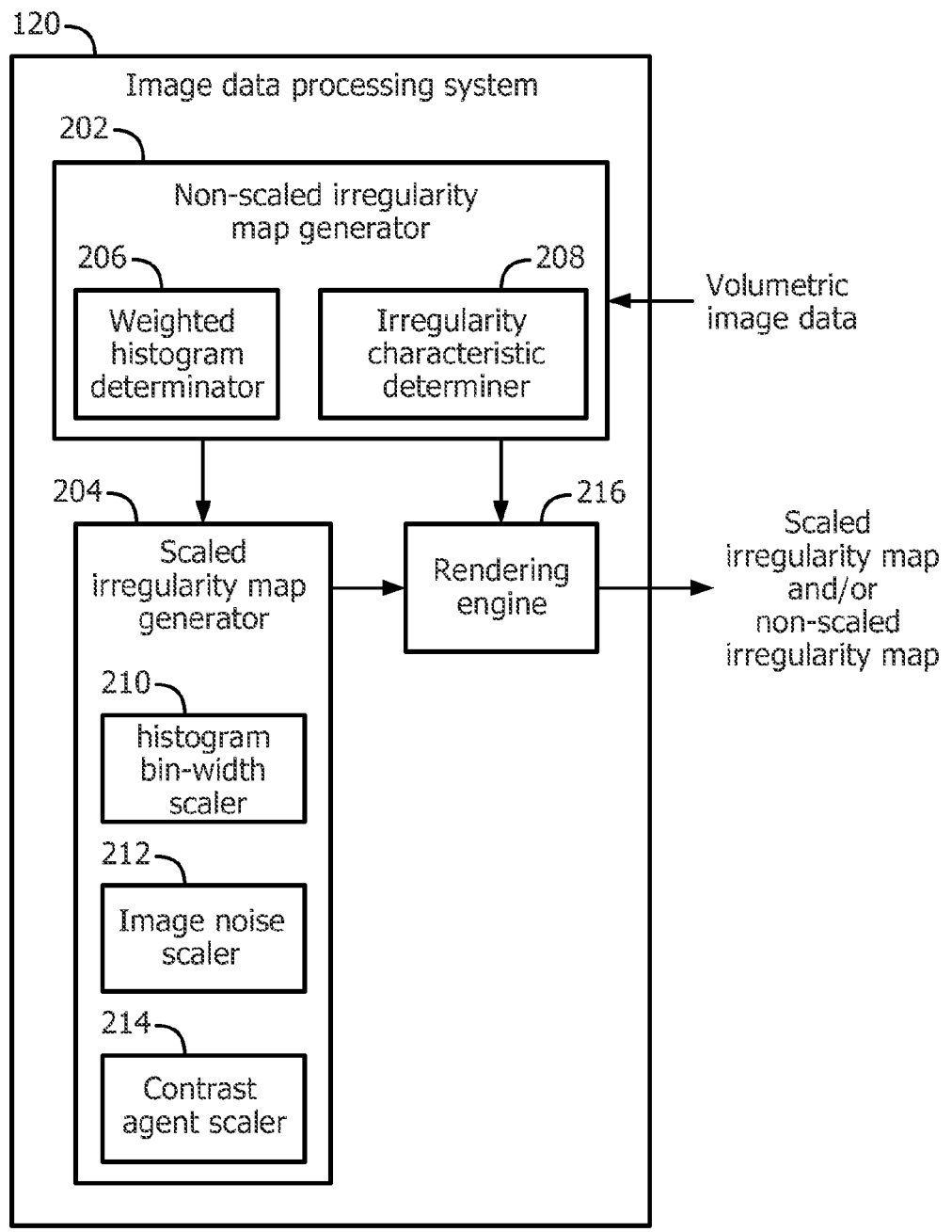

FIG. 2 schematically illustrates an example of the image data processing system 120. In this example, the image data processing system 120 obtains, as input, volumetric image data. The image data may represent one or more of anatomical or functional information, based on the imaging modality in use.

The illustrated image data processing system 120 includes a non-scaled irregularity map generator 202 and a scaled irregularity map generator 204, which scales a non-scaled irregularity map output of the non-scaled irregularity map generator 202 and/or otherwise generated. In a variation, the image data processing system 120 does not include the non-scaled irregularity map generator 202, but instead receives, as input, a non-scaled irregularity map, which is then scaled by the scaled irregularity map generator 204.

The non-scaled irregularity map generator 202 includes a weighted histogram determiner 206. The weighted histogram determiner 206 calculates, for each spatial position (e.g., an image voxel or pixel) in the volumetric image data (or a subset thereof, such as a region/volume of interest), a histogram that represents the weighted image information in a close surrounding of the analyzed spatial position. This is repeated, for example, to each voxel or each of a predetermined subset of voxels in the volumetric image data.

In one instance, the weighted histogram determiner 206 defines a mask of weights to weight the values of the surrounding voxels around a (central) voxel, which represents a currently analyzed position. For example, an appropriate mask can be a 3D Gaussian function with a defined sigma (width) value and/or a defined cut-off in a certain radius distance from the central voxel. The Gaussian width determines the histogram clustering length. By using the determined weights, a weighted histogram can be calculated. Example masks and histograms are shown in FIGS. 3 and 4.

Figure 3:
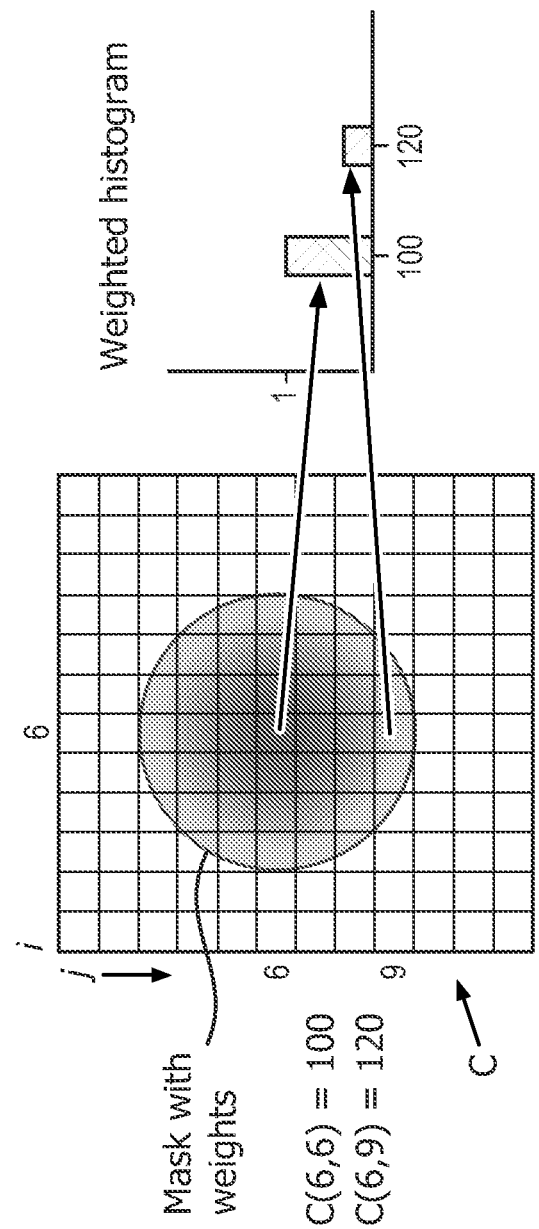
FIG. 3 illustrates an example 2D mask and 2D weighted histogram.
Figure 4:
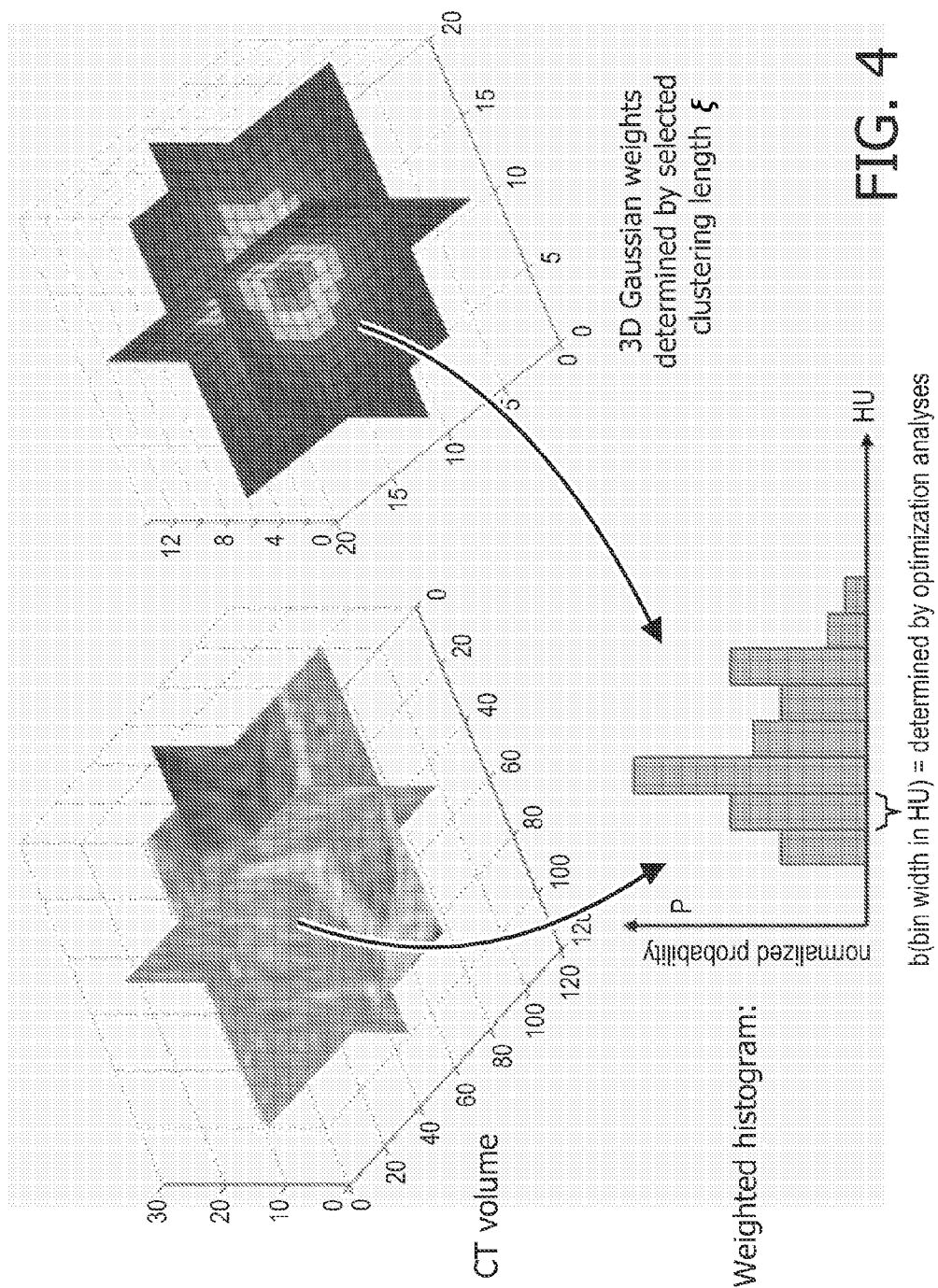
FIG. 4 illustrates an example 3D mask and 3D weighted histogram.

In FIGS. 3 and 4, the x-axis represents the Hounsfield unit (HU) value, and the y-axis represents the number of voxels for each HU value after multiplying the contribution of each voxel by a weight from the mask. As such, voxels in the close surrounding of the central voxel that are farther from central voxel will have a smaller contribution to the histogram relative to voxels in the close surrounding of the central voxel that are closer to central voxel. In this way, the weighting pattern, which is decreased gradually out of the central voxel, will contribute to smooth, less-patchy irregularity map.

More particularly, with respect to FIG. 3, an image C(i,j) is analyzed using a mask with weights (dark is a high value) centered on a voxel with (i,j) coordinates=(6,6) (all other voxels will be analyzed similarly). The weight in the center of the mask is =1, while the weight in the edge of the mask is =⅓. Two example image values C(6,6)=100 and C(6,9)=120 are mapped onto the histogram. The histogram y-axis values are weighted by the corresponding mask weights. FIG. 3 shows an example 2D mask and 2D histogram. An example 3D mask and 3D histogram is shown in FIG. 4.

A more detailed discussion of computing a weighted histogram is described in patent application Ser. No. 61/720,475, filed on Oct. 31, 2012, titled "Perfusion Imaging," and assigned to Koninklijke Philips Electronics N.V., which is incorporated by reference herein in its entirety. Other approaches to determining a weighted histogram are also contemplated herein.

In a more specific 3D example, a 3D Gaussian weight mask is defined for the surrounding voxels as: $W_0(i,j,k)=\exp(-(i^2 \cdot r_x^2+j^2 \cdot r_y^2+k^2 \cdot r_z^2)/2/\xi^2)$ where $[r_x, r_y, r_z]$ are the millimeter (mm)/pixel ratios in the image volume and [i,j,k] are those indexes (around [0,0,0]) for which $W_0$ is above a predetermined threshold. A normalized weight mask W can be derived to satisfy $\Sigma_v W_v=1$ where $W_v$ are all mask values. The Gaussian width $\xi$ (e.g., in mm) determines the histogram clustering length. The histogram bin partition in the relevant HU range is pre-defined.

The weighted histogram is constructed in a process in which each voxel which is covered by the mask (in the vicinity of the central voxel) adds the corresponding mask weight to the height of the histogram bin which comprises the image voxel HU value. As discussed above, in this way, the weighting pattern, which is decreased gradually out of the central voxel, will contribute to smooth and less-patchy irregularity map. The histogram is normalized to satisfy $\tau_i$ $p_i=1$, where i is the bin number and $p_i$ is the bin height.

Returning to FIG. 2, the non-scaled irregularity map generator 202 further includes an irregularity characteristic determiner 208, which determines one or more irregularity characteristics based on the local weighted histogram. In this example, the irregularity characteristic determiner 208 determines at least an entropy S of the normalized histogram. (Other characteristics may include, but are not limited to, uniformity, a spatial gray-level co-occurrence, etc.) The entropy represents irregularity or disorder and can be determined based on EQUATION 1:

$$S = -\sum_i p_i \log(p_i). \qquad \text{EQUATION 1}$$

The base of the log function can be set arbitrarily once (e.g. natural (e), etc.).

The scaled irregularity map generator 204 includes at least one of a histogram bin width-scaler 210, an image noise scaler 212 or a contrast agent scaler 214. The illustrated scaled irregularity map generator 204 includes all three. However, it is to be understood that this is for explanatory purposes and is not limiting. In other embodiment, only one, two or all three are included. In addition, in other embodiments, at least one other scaler is included, with or without 210, 212 and/or 214.

The histogram bin width-scaler 210 scales the irregularity map based on bin width, which may make the entropy calculation independent of the actual bin width, which may change from study to study. In this example, a suitable bin width scaling is shown in EQUATION 2:

$$S = -\sum_i p_i \log(p_i) + \log(b), \qquad \text{EQUATION 2}$$

where b is the histogram bin width in image value units (e.g., HU in CT) and can be determined as discussed below or otherwise. The log(b) term facilitates correcting for and maintaining the entropy, even if the bin-width is varied. This allows for calculating an approximately same entropy value, independent of the histogram bin width. As such, the bin width can change without affecting the entropy value.

Figure 5:
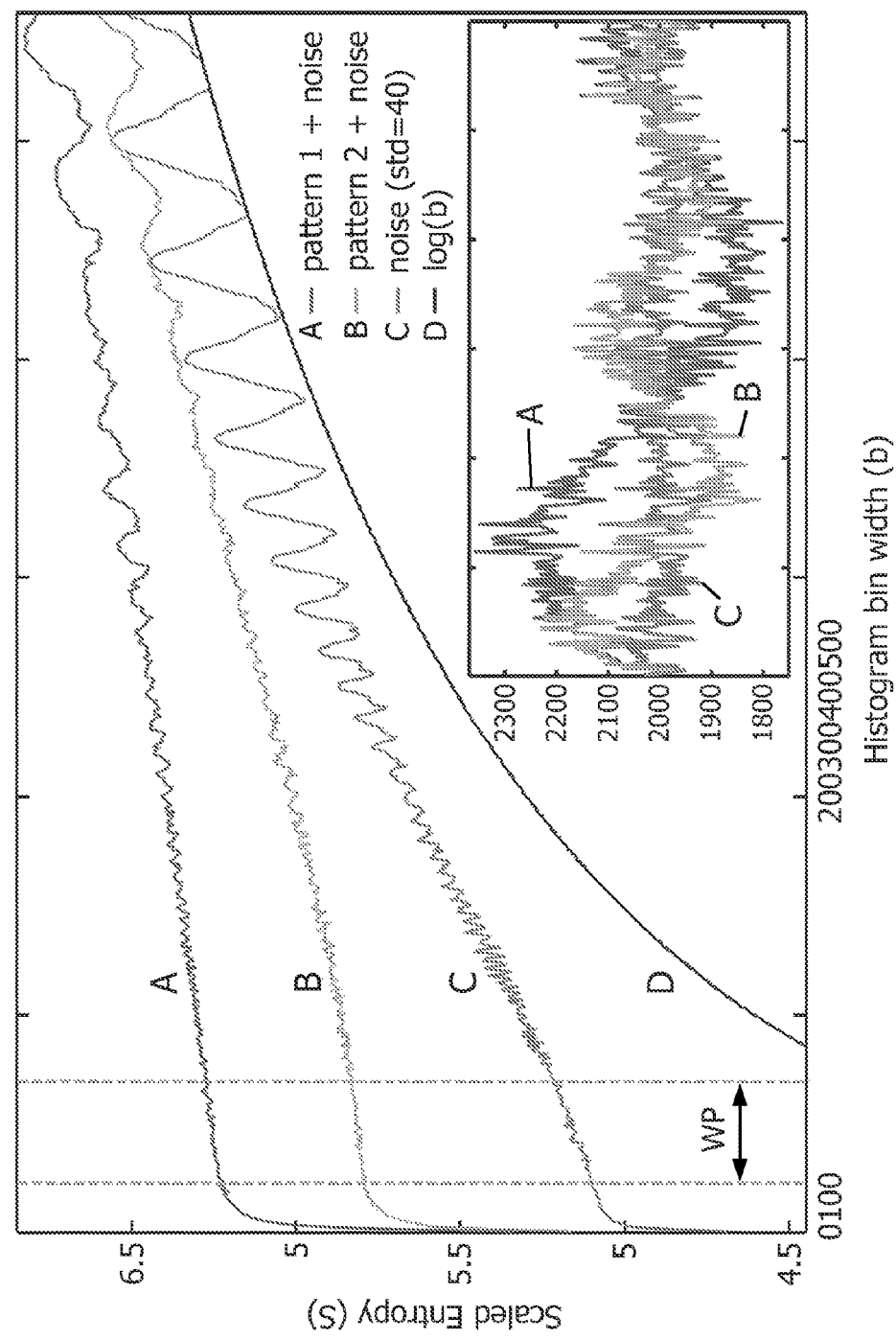
FIG. 5 illustrates the dependency of entropy on bin width.

This is shown in connection with FIG. 5, which shows synthetic simulation of the varying bin width effect. The optimal working-point range (WP) in this case is determined where the entropy of patterns 1 and 2 are nearly constant and the differences between their entropies to that of the noise are the largest, potentially giving the highest definition.

The optimal bin-width depends on several considerations. A lower bound can be set based on the fact that the maximal expected entropy of the image value distribution will be smaller than the maximal feasible calculated entropy, which is limited by the weight mask. A reasonable upper bound corresponds to the image noise. These conditions can be expressed as shown in EQUATION 3:

$$2std(\text{noise}) > b > (I_h - I_l) \cdot \exp\left(\sum_v W_v \log(W_v)\right), \qquad \text{EQUATION 3}$$

where $I_h$ and $I_l$ are the expected high and low limits (e.g. in HU in CT) of the image value distribution of interest. Since b depends overall on the image value range and noise, on the clustering length, and on the mm/pixel ratios, the optimal b value cannot be determined as an arbitrary constant for all cases.

The following is discussed with respect to an arbitrary image volume region covered by a 3D Gaussian mask. If the image values in this region are different for each voxel (i.e. maximum entropy), the entropy of the normalized histogram after weighting the image values by the mask weights will equal the entropy of the normalized mask values (without applying bin width scaling, i.e. as bin=1), as shown in EQUATION 4:

$$S_W = -\sum_{i,j,k} W_{i,j,k} \log(W_{i,j,k}), \qquad \text{EQUATION 4}$$

where $W_{i,j,k}$ are the mask weights in x,y,z directions.

The minimal bin width $b_{min}$ can be estimated in a way that the maximal entropy that can be possibly measured will not be greater than the maximal entropy available by using the specific mask. The maximal entropy available by the mask (if all image values are different one from the other) is just $S_W$ as above.

The maximal entropy that can be theoretically measured is received after dividing equally all image values within a range R to the number of histogram bins and then calculating the entropy (which in the particular case of equal bin heights is just the log of the number of bins), where $R=I_h-I_l$, or the distribution between the limits $I_h$ and $I_l$, for a certain region of interest for which the entropy of the image value distribution is being calculated. This renders the approximated condition shown in EQUATION 5:

$$\log\left(\frac{R}{b_{min}}\right) = S_W. \qquad \text{EQUATION 5}$$

The optimal bin width should be larger than $b_{min}$ by a determined factor f, as shown in EQUATION 6:

$$b_{optimal} = f \times b_{min} = f \times \frac{R}{e^{S_W}}. \qquad \text{EQUATION 6}$$

The value of f can be approximately in a range of two (2) to ten (10), for example, in order to generate useful clustering (binning) in the histogram. In CT for example, where the units of the image values are in integer HU, the lower limit of b can be set to b=1 or 2 HU. Where $b_{optimal} \leq std(\text{noise})$, there is no need to use $b_{optimal} \ll std(\text{noise})$, even if $b_{min}$ is very small (e.g. due to a large selected clustering length).

Since $S_W$ Depends on the Clustering Length $\xi$ (Defined in mm for Example) and the mm/pixel in x,y,z, the clustering length ξ should be large enough to enable sufficiently lower b and the required entropy dynamic range.

Optimizing both ξ and b can be based on criterion for maximizing a local entropy variance across a relevant ROI (for which small ξ is usually preferable) and, at a same time, to maximize a calculated mean local entropy across this region (for which large ξ is usually preferable). The two complementary conditions can form a figure of merit for finding the optimal ξ and b that will give the highest entropy (irregularity) definition as shown in EQUATION 7:

$$\underset{\xi,b}{\operatorname{argmax}}[\operatorname{var}(S(\xi, b)) \cdot \operatorname{mean}(S(\xi, b) - C_0)], \quad \text{EQUATION 7}$$

where S are the all local entropy map values in the ROI, and $C_0$ is a constant value which is estimated as the minimum of mean(S) which is still in a reasonable range.

EQUATION 7 finds the optimal compromise between the two contradictory conditions to find the best ξ and b that will give the highest definition (or significance) of the irregularity analysis. Stated another way, the optimal ξ and b, for a ROI, can be determined by determining the variance (var) (or alternatively the standard deviation) and the mean of the entropy map values and to select (e.g. iteratively) the values of b and ξ that maximize the product (var(S)·mean(S−$C_0$)) where S are the all local entropy map values in the ROI (S is after applying bin-width scaling).

This can be done automatically, semi-automatically or manually for each case and for a selected relevant region of interest in order to select the optimal parameters for the irregularity map calculation.

In order to avoid showing irregularity values of textures which has no clinical relevance, the image value range can be limited for the specific required analysis. For example, if lung tissue is analyzed in CT, bone HU values can be excluded or binned into the highest used histogram bin. As another example, HU values below approximately 100 HU (contain mainly air) can be skipped in order to speed the calculation time.

The image noise scaler 212 scales the irregularity map to compensate for image noise, which may result from the transmitted x-ray Poissonic noise (or quantum noise) and/or image reconstruction. In general, pre-smoothing or de-noising by using known techniques can be applied to optimize the structure/texture identification relative to the noise level (i.e. the effective SNR). However, in order not to eliminate by mistake or to over-smooth true anatomical features, some image noise may still remain even after applying a noise reduction scheme.

As such, the image noise scaler 212 scales the irregularity map values for any varying image noise levels (providing the relevant anatomical texture can be identified above the noise level). In order to calculate the correct noise scaling, a tissue region with a known or measurable texture entropy is compared with another region of homogeneous tissue on which the base image noise can be estimated. In one instance, the two regions are located in the scanned body in such a way that it is reasonable to assume that the noise in the homogeneous tissue also represents the noise in the examined tissue.

Regarding the histogram entropy, the effect of the noise is equivalent to a convolution of the noise histogram with the real tissue texture histogram. As an approximation for the scaling model, it can assume that the histogram of the noise is with a normal distribution (i.e. a Gaussian histogram shape). Also assumed is that the histogram of the tissue texture also has a normal distribution, although this may not be always the case (however, in some natural tissue textures the histogram distribution shape will be relatively close to Gaussian; or at least the bins can be re-ordered to give a similar shape).

With such assumptions, the tissue histogram (real texture+noise) is the convolution of two Gaussians which also resultant as a wider Gaussian shape. The Gaussian sigma (width) after the convolution is shown in EQUATION 8:

$$\sigma_{total} = (\sigma_{texture}^2 + \sigma_{noise}^2)^{1/2}. \quad \text{EQUATION 8:}$$

The difference between the total histogram to the texture histogram is similar to spanning the histogram bins by a factor of shown in EQUATION 9:

$$\sigma_{total}/\sigma_{texture} = \sigma_{total}/(\sigma_{total}^2 - \sigma_{noise}^2)^{1/2}. \quad \text{EQUATION 9:}$$

The texture entropy (after eliminating the estimated noise effect) can be represented as shown in EQUATION 10:

$$S_{texture} = S_{total} - \log(\sigma_{total}/(\sigma_{total}^2 - \sigma_{noise}^2)^{1/2}). \quad \text{EQUATION 10:}$$

The sigma values of 'total' and 'noise' can be estimated from the measured entropies of the examined tissue region and the noise region.

Considering Gaussian shapes, the entropy is proportional to the log (σ) before applying any bin width scaling. If the measured entropies are already after bin-width scaling, this can be eliminated through the following definitions: $\sigma_{total} = f \cdot \exp(S_{total} - \log(b))$ and $\sigma_{noise} = f \cdot \exp(S_{noise} - \log(b))$. With this, the texture entropy $S_{texture}$ can be calculated (without needing to know the proportional factor f since it will be canceled in the quotient of EQUATION 10, and f can be set to a value of one (1).

$\sigma_{total}$ can be calculated for each spatial location from the local entropy map values, and $\sigma_{noise}$ can be considered as a mean value calculated from the entropy map mean value of the ROI of the homogenous tissue. The equation for $S_{texture}$ can be further reduced to EQUATION 11:

$$S_{texture} = \frac{1}{2} \cdot \log(e^{2S_{total}} - e^{2S_{noise}}). \quad \text{EQUATION 11:}$$

With EQUATION 11, there is no need to know the bin-width in the entropy map calculation. With this scaling, values of $S_{texture}$ lower than zero can be clipped to zero for a meaningful value (i.e. the minimum possible entropy), and the correction is negligible for $S_{total}$ significantly larger than $S_{noise}$.

A more general and accurate scaling scheme with less assumptions, can be done by direct de-convolution (e.g. by MLEM technique) of the known given noise histogram shape from the true total histogram shape (i.e. this of the texture with added noise).

The contrast agent scaler 214 scales the irregularity map based on a concentration of contrast agent administered to a subject or object (e.g. Iodine in CT or Gadolinium in MRI). Where no contrast has been administered, the contrast agent scale 214 is not employed and/or omitted.

An example scenario of where the contrast agent scaler 214 can be employed follows. Consider a tissue region with no significant observable structures/textures while it is imaged without contrast agent (e.g. certain liver diseases) where the goal is to calculate the entropy of the local structures where it appears with contrast agent. In such case, the entropy values depend on the contrast agent concentration.

In principle, in a local region, only part of the voxels may be enhanced by the agent. This enhancement is dependent on the relative blood volume within a voxel. For those voxels which are enhanced, the contrast agent affects (i.e. when varying its concentration from low to high) the histogram as spanning the histogram values across more bins up to the maximal image value enhancement. The histogram spanning is approximately uniform on all bins in the new range that contains both partial volume voxels with partial contrast enhancement and voxels with tissue having varying relative blood volume.

Therefore, the contrast agent affects similarly as changing the bins width (i.e. proportional to multiplication by 1/b within the log in the entropy equation) for those image values above the base tissue value without contrast agent. Since not all the voxels within a local region always get contrast agent enhancement, an approximation can be used for a scaling purpose, the average contrast enhancement in a local region, for example after strong smoothing (e.g. as with a Gaussian filter having the sigma of the histogram spatial weighting).

Where a same tissue is imaged with two different concentration levels of contrast agent, and the goal is to compare the calculated local entropy maps of the two different scans, if the tissue physiology is the same between the two cases, any changes should be due to the different agent concentrations, and the entropy difference can be determined based on EQUATION 12:

$$S_{c1} - S_{c2} = \log\left(\frac{(\bar{I}_{c1} - \bar{I}_0)}{(\bar{I}_{c2} - \bar{I}_0)}\right), \quad \text{EQUATION 12}$$

where $S_{c1}$ and $S_{c2}$ are the calculated entropies for the two agent concentration cases, $\bar{I}_{c1}$ and $\bar{I}_{c2}$ are the local "mean" image values from the smoothed images, and $\bar{I}_0$ is the base mean image value without contrast agent. Generally, EQUATION 12 holds because the relative "histogram bin spanning" between the two cases is proportional to the ratio between the two contrast agent concentrations (image value enhancement) above the base image values (without agent).

A general scaling scheme for any contrast enhanced scan is shown in EQUATION 13:

$$S_{contrast\_scaled}(c) = S_{measured}(c) - \log(\bar{I}_c - \bar{I}_0) \quad \text{EQUATION 13:}$$

This approach may be also applicable for a case where the tissue has an observable structure even without a contrast agent, but where a contrast agent is administered, all the tissue components get the same relative enhancement (i.e. as a single multiplication factor). This may be the case for example with a mesh of lung blood vessels or lung parenchyma.

A rendering engine 216 renders the scaled and/or non-scaled irregularity maps via the display 122 (FIG. 1). In one instance, the rendering engine 216 visually presents an irregularity map (scaled and/or non-scaled) side by side with the volumetric image data. In another instance, the rendering engine 216 visually presents the irregularity map (scaled and/or non-scaled) fused or superimposed with the volumetric image data. This may be similar to that done in multi-modality imaging (e.g. functional and anatomical images).

Furthermore, one or more color maps can be used for the irregularity maps. An entropy color-bar scale can be shown on, or near, the image while indicating the values corresponding to the scale limits, log of the bin-width, estimated image noise entropy, and the upper dynamic range limit according to the calculation parameters. Any clinically relevant texture value with reliable definition should be in the range between the estimated image noise entropy and the dynamic range limit.

One or both (individually or concurrently) of the scaled irregularity map or the non-scaled irregularity map can be visually presented. The scaled irregularity map may be scaled using all three scalings described herein (i.e., bin width, noise and contrast agent) or a subset thereof (e.g., by applying bin-width scaling and contrast-scaling, but not noise scaling). The non-scaled entropy map can be used anyhow for review, and the contrast-scaled map can be used for comparison with follow-up scans for example, and/or otherwise.

The approach described herein can be applied uniformly on the whole image volume without considering specific texture properties. However, more sophisticated options can include: A) identifying local sharp edges with clear directionality such as in tissue-bone interface or tissue-air interface and exclude them from the irregularity map, and/or B) interpreting irregularity from local image gradients and analyzing the histogram of the first derivative of the local image values.

After an irregularity map (scaled and/or non-scaled) is available, any ROI or VOI based analysis of the map values can be made, such as calculating the mean entropy an d its standard deviation within a region of interest selected by the user.

The above is discussed with respect to entropy. However, other approaches such as variations based on known texture analysis techniques, are also contemplated herein. Several known functions can be strongly correlated with the entropy measure since they also represent irregularity and heterogeneity. Therefore, scaling transformations (for bin-width, image noise, and/or contrast agent concentration) may be based on these functions, in accordance with disclosure described herein.

By way of non-limiting example, a uniformity function can be applied directly on the described weighted histogram. An example of a suitable uniformity function, also known as the 'energy function', is shown in EQUATION 14:

$$U = \sum_i (p_i)^2 \quad \text{EQUATION 14}$$

The irregularity measure can be expressed as the inverse of the uniformity (i.e. 1/U) instead of EQUATION 1. An example of this is discussed in published patent application US 2010/0142775 to Ganeshan et al.

By way of another non-limiting example, a Spatial gray-level co-occurrence-matrix (GLCM) can be used to estimate image properties related to high-order statistics. For this, each element (i,j) in the GLCM specifies a number of times that a pixel with gray-level value i occurred adjacent to a pixel with value j at a given offset ($\Delta x, \Delta y$). The GLCM matrix is a representation of a high-order histogram. An example of this is discussed in Pang et al., "Computerized segmentation and characterization of breast lesions in dynamic contrast-enhanced MR images using fuzzy c-means clustering and snake algorithm", Computational and Mathematical Methods in Medicine (2012), and in Mitrea at al., "Abdominal tumor characterization and recognition using superior-order co-occurrence matrices, based on ultrasound images", Computational and mathematical methods in medicine (2012).

Several mathematical functions based on the 'entropy', the 'inverse of uniformity', the 'information measure of correlation' applied on the GLCM elements, and/or other approach can represent irregularity and heterogeneity and therefore can be correlated with the entropy function described herein. In addition, the local weighting of the high-order histogram can be done in the same manner as the local weighting process described herein. The scaling of the high order functions can be done in the same manner as the scaling steps described herein.

Figure 6:
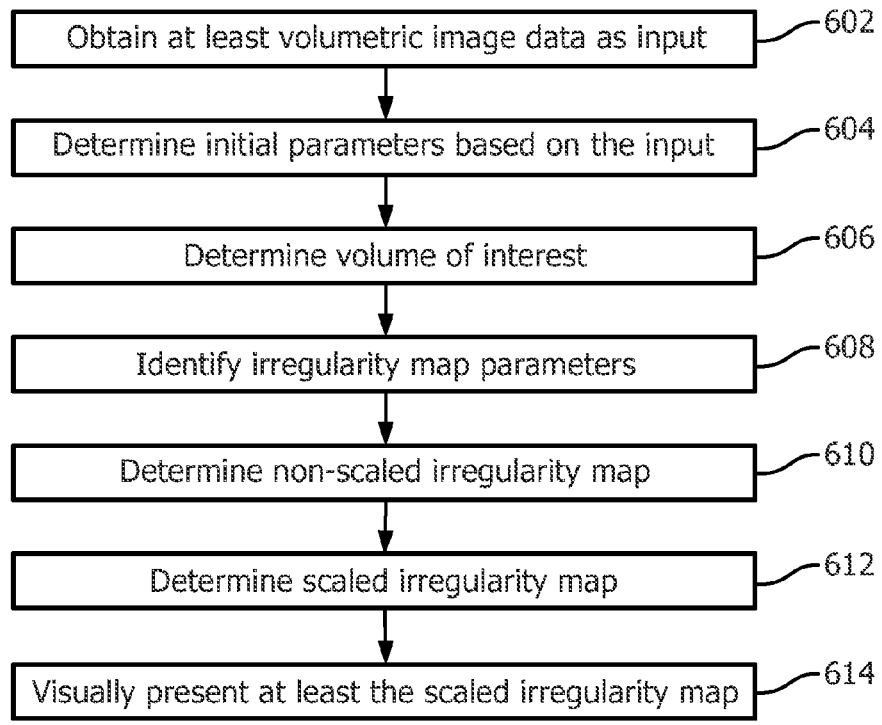
FIG. 6 illustrates a method for generating a scaled irregularity map for image data.

FIG. 6 illustrates a method for generating a scaled (bin width, noise and/or contrast agent) irregularity map for image data.

It is to be appreciated that the ordering of the acts is not limiting. As such, other orderings are contemplated herein. In addition, one or more acts may be omitted and/or one or more additional acts may be included.

At 602, volumetric image data is obtained. As discussed herein, this data can be obtained from the imaging system 100, other system, and/or a data repository. Optionally, in addition to the volumetric image data, different volumes from different scans (e.g., follow-up, etc.) can be obtained. Optionally, in addition to the volumetric image data, parameters and results from one or more previous irregularity map analysis of one or more preceding scans can be obtained.

At 604, initial parameters are determined based on the obtained data. Optionally, before act 604, at least one of noise reduction, smoothing, or image resampling can be performed on the obtained data.

At 606, a volume of interest is identified. This may include the entire scanned volume or a subset thereof and can be performed automatically, semi-automatically or manually. Where the entire scanned volume is of interest, this act can be omitted.

At 608, irregularity map parameters of interest are identified. This may include optimization of weighted-histogram clustering length, histogram bin width, image value bin range, etc.

At 610, a non-scaled irregularity map is generated. As described herein, this can be based on entropy, uniformity, GLCM and/or other approach correlated to irregularity and heterogeneity.

At 612, a scaled irregularity map is generated based on the non-scaled irregularity map. As described herein, one or more of bin width, noise and/or contrast agent scaling can be applied to the non-scaled irregularity map.

At 614, at least one of the scaled irregularity map or the non-scaled irregularity map is visually presented, with or without the image data.

Optionally, a region of interest based analysis, as discussed herein, is performed on at least the scaled irregularity map.

Optionally, at least the scaled irregularity map is stored and utilized in connection with a subsequent irregularity map determination.

Figure 7:
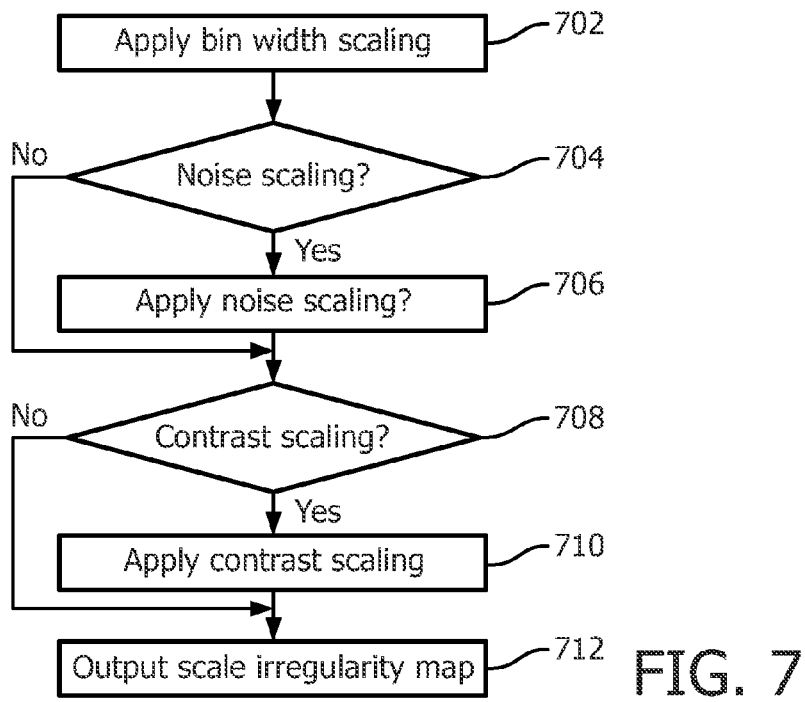
FIG. 7 illustrates a method for scaling the irregularity map in FIG. 6.

FIG. 7 illustrates a non-limiting method for implementing act 612 of FIG. 6.

It is to be appreciated that the ordering of the acts is not limiting. As such, other orderings are contemplated herein. In addition, one or more acts may be omitted and/or one or more additional acts may be included.

At 702, bin width scaling is applied, as described herein, to the non-scaled irregularity map, thereby generating a (bin width) scaled irregularity map.

At 704, it is determined whether noise scaling will be applied to the scaled irregularity map.

If so, then at 706, noise scaling is applied, as describe herein, to the scaled irregularity map, further scaling the irregularity map.

If not, then noise scaling is not performed.

In either circumstance, at 708, it is determined whether contrast scaling will be applied to the scaled irregularity map.

If so, then at 710, contrast scaling is applied, as described herein, to the scaled irregularity map, further scaling the irregularity map.

If not, then contrast scaling is not performed.

In either circumstance, at 712, at least the scaled irregularity map is output.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
obtaining a non-scaled irregularity map generated based on local weighted histograms of voxel distributions about voxels of interest from volumetric image data of a subject or object, wherein the local weighted histograms include a plurality of bins having a predetermined bin width, and wherein the local weights are determined based on a predetermined cluster length; and
scaling the non-scaled irregularity map, generating a scaled irregularity map, wherein the non-scaled irregularity map is scaled based at least on the histogram bin width.

2. The method of claim 1, further comprising:
representing the scaled irregularity map through an entropy value.

3. The method of claim 1, further comprising:
representing the scaled irregularity map through one or more of an inverse of a uniformity of the local weighted histogram or high-order statistics of local weighted high-order histogram, where the high-order histogram is based on co-occurrence matrix, and the high-order statistics include entropy or inverse of uniformity functions.

4. The method of claim 1, further comprising:
scaling the non-scaled irregularity as a function of a logarithm of the histogram bin width.

5. The method of claim 1, wherein the scaled irregularity map is independent of the histogram bin width.

6. The method of claim 1, wherein the predetermined bin width and the predetermined cluster length are optimized to give the highest definition of the irregularity maps.

7. The method of claim 6, further comprising:
estimating a minimum bin width such that a maximum measurable entropy is equal to or less than a maximum available entropy due to use of a specific histogram weight mask and a maximal range of image values.

8. The method of claim 6, further comprising:
determining a maximum bin width of interest based on image noise.

9. The method of claim 6, further comprising:
determining optimal bin width and optimal cluster length based on maximizing a product of a variance and a shifted mean of the irregularity map values.

10. The method of claim 1, further comprising:
scaling the non-scaled irregularity map based on an image noise.

11. The method of claim 10, further comprising:
scaling the non-scaled irregularity map by direct deconvolution of a given noise histogram from a total histogram, which is a real texture histogram with added noise.

12. The method of claim 1, further comprising:
scaling the non-scaled irregularity map based a contrast agent concentration.

13. The method of claim 12, further comprising:
scaling the non-scaled irregularity map as a function of a negative log of a difference between an average image values of a contrast scan and an average image values of a non-contrast scan.

14. The method of claim 1, further comprising:
visually presenting at least one of the scaled irregularity map or the non-scaled irregularity map either side by side with the volumetric image data or fused with the volumetric image data.

15. The method of claim 1, further comprising:
visually presenting at least one of the scaled irregularity map or the non-scaled irregularity map using a color map along with a color-bar scale.

16. The method of claim 1, further comprising:
visually presenting a value indicative of at least one scale limits, a log of the bin-width, an estimated image noise entropy, or an upper dynamic range limit.

17. The method of claim 1, further comprising:
performing a region or volume of interest analysis of the irregularity map values.

18. The method of claim 1, further comprising:
calculating a mean irregularity map value and a corresponding standard deviation within a region or volume of interest.

19. An image data processing system, comprising:
a scaled irregularity map generator that obtains a non-scaled irregularity map generated based on local weighted histograms of voxel distributions about voxels of interest from volumetric image data of a subject or object, wherein the local weighted histograms include a plurality of bins having a predetermined bin width and a predetermined cluster length, the scaled irregularity map generator, including:
a histogram bin-width scaler that scales the non-scaled irregularity map, generating a scaled irregularity map, wherein the non-scaled irregularity map is scaled based at least on one of the histogram bin width, an image noise or a contrast agent concentration.

20. The system of claim 19, wherein the scaled irregularity map is represented via one or more of an entropy or an inverse of uniformity of the local weighted histogram, or high-order statistics of local weighted high-order histogram.

* * * * *